US005698182A

United States Patent [19]
Prencipe et al.

[11] Patent Number: 5,698,182
[45] Date of Patent: Dec. 16, 1997

[54] DENTIFRICE COMPOSITION CONTAINING CALCIUM PEROXIDE HAVING HEIGHTENED TOOTH WHITENING EFFECT

[75] Inventors: Michael Prencipe, West Windsor; James G. Masters, Flemington; Vincent O. Drago, Sayreville, all of N.J.

[73] Assignee: Colgate Palmolive Company, New York, N.Y.

[21] Appl. No.: 735,163

[22] Filed: Oct. 22, 1996

Related U.S. Application Data

[63] Continuation-in-part of Ser. No. 340,568, Nov. 14, 1994, Pat. No. 5,599,527.

[51] Int. Cl.$^6$ ............................ A61K 7/16; A61K 7/20
[52] U.S. Cl. .................................. 424/53; 424/49
[58] Field of Search ............................ 424/49–88

[56] References Cited

U.S. PATENT DOCUMENTS

| | | | |
|---|---|---|---|
| 5,565,190 | 10/1996 | Santalucia et al. | 424/53 |
| 5,571,501 | 11/1996 | Toy | 424/47 |
| 5,599,525 | 2/1997 | Hsu et al. | 424/53 |
| 5,599,527 | 2/1997 | Hsu et al. | 424/53 |
| 5,614,174 | 3/1997 | Hsu et al. | 424/53 |
| 5,648,064 | 7/1997 | Gaffar et al. | 424/53 |

*Primary Examiner*—Shep K. Rose
*Attorney, Agent, or Firm*—Paul Shapiro

[57] ABSTRACT

A method for inhibiting dental calculus concomitant with tooth whitening is disclosed wherein there is applied to the teeth an oral composition containing in a vehicle an amount of a anticalculus phosphate salt and an amount of calcium peroxide effective to whiten teeth, the vehicle containing about 4 to about 9% by weight water and an amount of calcined alumina effective to heighten the whitening effect of the $CaO_2$, and allowing the composition to remain on the teeth for a time sufficient to effect whitening thereof.

11 Claims, No Drawings

DENTIFRICE COMPOSITION CONTAINING CALCIUM PEROXIDE HAVING HEIGHTENED TOOTH WHITENING EFFECT

This application is a continuation-in-part of U.S. Ser. No. 340,568 filed Nov. 14, 1994, now U.S. Pat. No. 5,599,527.

FIELD OF THE INVENTION

This invention relates generally to an oral composition which when applied onto the surface of teeth acts to whiten teeth and more particularly to an oral composition for whitening teeth that is more effective than existing products.

THE PRIOR ART

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth.

In copending patent application U.S. Ser. No. 340,558 now U.S. Pat. No. 5,599,527 there is disclosed a storage stable dentifrice composition for cleaning teeth containing bicarbonate and peroxide ingredients such as sodium bicarbonate and calcium peroxide, and an effective anticalculus combination of about 0.5 to about 2% by weight of a water soluble pyrophosphate, about 0.5 to about 3% by weight of a water soluble polyphosphate salt.

Although the dentifrice composition disclosed in U.S. Ser. No 340,568 now U.S. Pat. No. 5,599,527, is effective in inhibiting calculus formation, the composition exhibits limited effectiveness in whitening teeth inspite of the presence of calcium peroxide in the composition. It is therefore desirable to heighten the whitening efficacy of the calcium peroxide containing anticalculus dentifrice.

SUMMARY OF THE INVENTION

In accordance with the present invention there is provided a method of whitening stained or discolored teeth wherein there is applied to teeth in the oral cavity an oral composition comprising a vehicle containing an amount of a phosphate salt effective to inhibit dental calculus and an amount of calcium peroxide effective to whiten teeth, the vehicle containing about 4 to about 9% by weight water and an amount of calcined alumina effective to heighten the whitening effect of the $CaO_2$ and thereafter allowing the composition to remain on the teeth for a time sufficient to effect whitening thereof.

DESCRIPTION OF THE PREFERRED EMBODIMENTS

The vehicle used in the preparation of the calcium peroxide containing dentifrice is formulated to impart to the dentifrice the pasty consistency, body and non-tacky nature which is characteristic of conventional dental creams or gels. As is well known, such pastes and gels are extrudable from ordinary collapsible toothpaste tubes to forms a ribbon of substantial thickness, e.g., about 0.5 to 1 cm. which if left undisturbed, substantially retains its original thickness over a period of one minute or more and does not penetrate substantially into the bristles of a toothbrush when resting on the ends of such bristles for a similar period.

The dentifrice vehicle includes a suitable humectant which is a substantially anhydrous viscous material, such as glycerin, propylene glycol, or any suitable mixture thereof. Water is included in the dentifrice in an amount of no more than about 9% by weight of the composition and no less than about 4% by weight of the composition. Preferably water is present in the dentifrice at a concentration of about 5 to about 8% by weight. When water is present in the dentifrice in an amount in excess of about 9% by weight, e.g., 10% by weight, the stability of the dentifrice is adversely affected whereby on storage at elevated temperatures, e.g., 105° F., the peroxide dissociates and the gas formed bloats the tube in which the dentifrice is packaged aerating the dentifrice product creating an unacceptable "cheesy" appearance. At water concentrations less than about 4% by weight the dentifrice exhibits marginally acceptable rheological properties primarily poor consistency, due to the fact that the gums conventionally used as thickeners do not properly hydrate in the peroxide containing dentifrice at such low water concentrations.

The proportion of vehicle in the dentifrice of the present invention is generally within the range of about 40 to about 70% by weight of the dentifrice and preferably about 50 to about 65% by weight of the dentifrice. Glycerin is present in the dentifrice vehicle of the present invention at a concentration of about 10 to about 60% by weight and preferably about 15 to about 40% by weight and propylene glycol is present in the vehicle at a concentration of about 1 to about 5% by weight and preferably 2 to 4% by weight.

A surfactant is used in the preparation of dentifrice composition of the present invention to aid in thorough dispersion of the dentifrice composition throughout the oral cavity when applied thereto as well as to improve the cosmetic acceptability and detersive and foaming properties of the dentifrice. Among the organic surfactants useful in the practice of the present invention are salts of the higher alkyl sulfates, such as sodium lauryl sulfate (SLS) or other suitable alkyl sulfate having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isothionic acid or with glycerol monosulfate, such as the sodium salt of monosulfated monoglyceride of hydrogenated coconut oil fatty acids; salts of olefin sulfonates, e.g., alkene sulfonates or hydroxylakene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium, potassium or mono-, di or triethanol amine.

The surfactant is included in the dentifrice vehicle of the present invention at a concentration of about 0.5 to about 3.0% by weight and preferably about 1.0 to about 2.0% by weight.

Abrasives, in addition to calcined alumina, may be incorporated in the dentifrice. These abrasives include precipitated amorphous hydrated silica, such as Sorbosil AC-35 marketed by Crosfield Chemicals, or Zeodent 115 from J.M. Huber Company, sodium metaphosphate, potassium metaphosphate, tricalcium phosphate, calcium phosphate dihydrate, anhydrous dicalcium phosphate, calcium pyrophosphate, sodium bicarbonate, calcium carbonate and calcined alumina. As will hereinafter be demonstrated, the presence of calcined alumina in the dentifrice produces unexpected improvement on whitening.

The total abrasive content incorporated in the dentifrice composition of the present invention is present at a concentration of about 10 to about 30% by weight and preferably 15 to about 25% by weight. Calcined alumina is present in the dentifrice composition at a concentration of about 2 to about 30% by weight and preferably about 5 to about 20% by weight whereby a heightened tooth whitening effect is obtained.

Inorganic thickeners may be included in the dentifrices of the present invention and include fumed silicas such as Cabosil available from Cabot Corporation, and thickening silicas including those available from J. M. Huber designated Zeodent 165. Organic thickeners such as natural and synthetic gums and colloids may also be incorporated in the dentifrice composition of the present invention. Examples of such thickeners include carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose (co-dried blends of microcrystaline cellulose/cellulose gum).

The inorganic or organic thickener may be incorporated in the compositions of the present invention at a concentration of about 0.05 to about 2% by weight and preferably about 0.1 to about 1.5% by weight.

The calcium peroxide compound to function as a whitening agent is incorporated in the dentifrice of the present invention, at a concentration of about 0.10 to about 5% by weight and preferably about 0.5 to about 2.0% by weight.

A water soluble alkali metal compound is included in the dentifrice composition to inhibit the formation of undesirable gaseous products during storage when sodium bicarbonate is present in the dentifrice. Examples of such alkali metal compounds include alkali metal hydroxides, carbonates, sesquicarbonates, borates and silicates specific examples of which are sodium hydroxide, potassium hydroxide, sodium carbonate, potassium carbonate, sodium borate, sodium sesquicarbonate and sodium silicate. The water soluble alkali metal compound is incorporated in the dentifrice composition of the present invention at concentrations in the range of about 0.5 to about 3.0% by weight and preferably about 1.0 to about 2.0% by weight.

Fluoride-providing salts having anti-caries efficacy may also be incorporated in the oral compositions of the present invention and are characterized by their ability to release fluoride ions in water. It is preferable to employ a water-soluble salt fluoride providing about 10 to 5,000 ppm of fluoride ion and preferably about 1000–1500 ppm of fluoride ion. Among these materials are water-soluble alkali metal salts, for example, sodium fluoride, potassium fluoride, sodium monofluorophosphate and sodium fluorosilicate. Sodium monofluorophosphate is the preferred fluoride-providing salt.

Salts effective in inhibiting the formation of dental calculus include water soluble phosphate salts, such as dialkali or tetra-alkali metal pyrophosphate salts such as $Na_4P_2O_7$ $K_4P_2O_7$, $Na_2K_2P_2O_7$, $Na_2H_2P_2O_7$ and $K_2H_2P_2O_7$, long chain polyphosphate such as sodium hexametaphosphate and cyclic phosphates such as sodium trimetaphosphate as well as alkali metal tripolyphosphates such as sodium tripolyphosphate (STPP) and potassium tripolyphosphate may be incorporated in the dentifrice compositions of the present invention at a concentration of about 0.5 to about 8.0% by weight. Preferably, the anticalculus salt is present in the dentifrice composition as a mixture of $Na_4P_2O_7$ (TSPP) or $K_4P_2O_7$ (TKPP) and sodium tripolyphosphate (STPP) wherein the TSPP or TKPP is present at a concentration of about 0.5 to about 2% by weight and the STPP is present at a concentration of about 1 to about 3% by weight.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5–1000 microns, preferably 250–500 microns, and are present at a concentration of 0.5 to 3% by weight. Dyes are generally sensitive to the presence of the peroxide ingredient and are not included in the dentifrice although FD&C Green #3 has been found to be resistant to fading when $CaO_2$ is present in the dentifrice.

Any suitable flavoring or sweetening material may be employed. Examples of suitable flavoring ingredients are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the oral composition components of this invention. Non-limiting examples thereof include preservatives, silicones and chlorophyll compounds, vitamins such as vitamins B6, B12, C, E and K, antibacterial agents such as chlorohexidene, halogenated diphenyl ethers such as triclosan, desensitizing agents such as potassium nitrate and potassium citrate and mixtures thereof. These adjuvants are incorporated in the dentifrice in amounts which do not substantially adversely affect the properties and characteristics desired, and are selected and used in proper amounts, depending upon the particular type of component involved.

To prepare the dentifrice composition of the present invention, the humectants, e.g., glycerin, propylene glycol, sweetener and water are dispersed in a conventional mixer until the mixture becomes a homogeneous gel phase. Into the gel phase are added a pigment such as $TiO_2$ and any anticalculus agents such as tetrasodium pyrophosphate or sodium tripolyphosphate or both and afluoride anti-caries agent such as or sodium monofluorophosphate. These ingredients are mixed until a homogeneous phase is obtained. Thereafter the thickener, abrasives, peroxide, flavor and surfactant ingredients are added and the ingredients mixed at high speed under vacuum of about 20–100 mm Hg. The resultant product is a homogeneous, semi-solid, extrudable paste product.

The following examples are further illustrative of the present invention, but it is understood that the invention is not limited thereto. All amounts and proportions referred to herein and the appended claims are by weight.

EXAMPLE

A dentifrice composition of the present invention designated "Composition A" was prepared containing CaO₂ and calcined alumina as ingredients as set forth in Table 1 below.

For purposes of comparison, the procedure of the Example was repeated except that calcined alumina was not included in the dentifrice (Composition B) or hydrated alumina was substituted for calcined alumina (Compositions C). The ingredients of Compositions B and C are also listed in Table I.

TABLE I

Dentifrice Compositions

| Ingredients | A Wt. % | B Wt. % | C Wt. % |
|---|---|---|---|
| Deionized Water | 6.00 | 10.00 | 6.00 |
| Glycerin | 25.5 | 26.00 | 25.5 |
| Propyene Gycol | 14.39 | 12.89 | 14.39 |
| Sodium Bicarbonate | 12.00 | 16.00 | 12.00 |
| Calcined Alumina | 10.0 | 0.0 | 0.0 |
| Hydrous Alumina | 0.0 | 0.0 | 10.00 |
| Carboxymethyl Cellulose | 0.2 | 0.2 | 0.2 |
| Carrageenan | 0.2 | 0.2 | 0.2 |
| Sodium Monofluorophosphate (MFP) | 0.76 | 0.76 | 0.76 |
| Tetrasodium Pyrophosphate (TSPP) | 2.00 | 2.00 | 2.00 |
| Sodium Tripolyphosphate (STPP) | 3.00 | 3.00 | 3.00 |
| TiO₂ | 2.00 | 2.00 | 2.00 |
| Hydrated Silica (Zeodent 115) | 16.50 | 20.00 | 16.50 |
| Zeodent 165 (Amorphous Silica) | 2.00 | 1.50 | 2.00 |
| Sodium Lauryl Sulfate | 1.50 | 1.50 | 1.50 |
| Calcium Peroxide | 1.00 | 1.00 | 1.00 |
| Na Saccharin | 0.50 | 0.50 | 0.50 |
| NaOH | 1.50 | 1.50 | 1.50 |
| Flavor | 0.95 | 0.95 | 0.95 |
| Total | 100.00 | 100.00 | 100.00 |

Procedure

To prepare the dentifrices, the carboxymethyl cellulose and carrageenan gums were dispersed in the formula amount of glycerin. MFP and saccharin were dissolved in a formula amount of water which was then added to the gum dispersion, mixed and heated to 140° F. for 15 minutes. The propylene glycol, TSPP, STPP and NaOH were added sequentially, and mixed for an additional 20 minutes. The dispersion was transferred to a vacuum mixer, and the siliceous agent, baking soda, calcined alumina or hydrated alumina, CaO₂, SLS and flavor were added and mixed for 10–30 minutes at high speed under vacuum to obtain a homogeneous mixture. The resultant product was a paste with satisfactory flavor and was white in color.

To test the whitening efficacy of the dentifrice, bovine permanent central incisors are cut to obtain labial enamel specimens approximately 10 mm² in accordance with the procedure described in Stookey et al, "In Vitro Removal of Stain with Dentifrice", J. Dent. Res. 61 (11):1236–1239, November, 1982.

The enamel specimens were mounted in a staining apparatus constructed to provide alternate immersion of the specimens into a staining broth consisting of finely-ground instant coffee, instant tea and gastric mucin dissolved in 800 ml (milliliters) of sterilized trypticase soy broth. Twenty-six ml of a 24-hour Sarcina lutea turtox culture was also added to the staining broth. The apparatus, with the enamel specimens attached and the staining broth in place was then placed in an incubator (37° C.) with the specimens rotating continuously through the staining broth and air. The staining broth was replaced twice daily for four consecutive days. With each broth change, the trough and specimens were rinsed with deionized water to remove any loose deposits. After the four-day staining period, a darkly-stained film or coating was apparent on the enamel surfaces. Thereafter the specimens were removed from the staining apparatus, rinsed and air dried and then refrigerated until used.

To test each dentifrice for whitening effect, eight stained specimens were divided and mounted on a brushing machine equipped with soft nylon toothbrushes adjusted to 150 gram tension on the enamel surface. The enamel specimens were brushed for 200 strokes using 2% sodium carboxymethyl cellulose solution to remove any loose stains from the enamel surface. The specimens were then brushed with the dentifrice slurry consisting of 1 part toothpaste, 1 part water for 300 strokes. The specimens were then cleaned with pumice flower for one minute or until all stain was removed. Reflectance measurements were taken using a Minolta Chroma Meter (Model CR 321) after pre-brushing, brushing and pumicing of the bovine enamel specimens. The CIE L* a* b* scale was chosen to measure the color of the teeth. The percent stain removed is then calculated as follows:

$$\% SR = \frac{SQRT((L_2^* - L_1^*)^2 + (a_2^* - a_1^*)^2 + (b_2^* - b_1^*)^2)}{SQRT((L_3^* - L_1^*)^2 + (a_3^* - a_1^*)^2 + (b_3^* - b_1^*)^2)} \times 100$$

where $L_1^*$, $a_1^*$, and $b_1^*$ are reflectance measurements taken after the pre-brush step, $L_2^*$, $a_2^*$ and $b_2^*$ are reflectance readings taken after brushing, and $L_3^*$, $a_3^*$, and $b_3^*$ are measurements taken after pumicing. The % SR value determined for each of the dentifrices tested is recorded in Table II below.

TABLE II

| Composition | Percent Stain Removal |
|---|---|
| A | 73 |
| B | 44 |
| C | 45 |

The % SR values recorded in Table II indicate that the presence of calcined alumina substantially increased the tooth whitening efficacy of CaO2 by about 66% when compared to dentifrices in which the calcined alumina was absent and inspite of the presence of other abrasive materials including hydrated alumina.

To determine the effect on aging at elevated temperatures of the dentifrice of the present invention, a series of toothpastes having the composition of Composition A but containing varying amounts of water (6–10%) packed in collapsible laminate tubes, were exposed to heated air at 105° F. for a period of 12 weeks. Attempts to prepare Composition A with 4% by weight water produced a marginally acceptable dentifrice composition as the gums present did not hydrate properly with the result that the dentifrice had rheological properties of borderline acceptability.

The aging stability results are recorded in Table III below.

TABLE III

Aging Study of Composition A

| % Water in Composition A | Fluoride Stability 4 Weeks @ 105° F. | Peroxide Stability 12 weeks @ 105° F. |
|---|---|---|
| 6% | 100% | 87% |
| 8% | 98% | 81% |
| 10% | 88% | Cheesy @ RT after few days |

The results recorded in Table III indicate an optimum level of water (<10%) is needed in the dentifrice of the present invention in order to obtain satisfactory fluoride and peroxide aging stability.

We claim:

1. A method of inhibiting dental calculus concomitant with whitening stained or discolored teeth which comprises applying to such teeth in the oral cavity an oral composition containing in a vehicle an amount of calcium peroxide effective to whiten teeth, the vehicle containing about 4 to about 9% by weight water, phosphate salt effective to inhibit dental calculus and an amount of calcined alumina effective to heighten the whitening effect of the CaO2, and then allowing the composition to remain on the stained teeth for a time sufficient to effect whitening thereof.

2. The method of claim 1 wherein water is present in the dentifrice at a concentration of about 5 to about 8% by weight.

3. The method of claim 1 wherein the $CaO_2$ is present in the dentifrice at a concentration of about 0.1 to about 3% by weight.

4. The method of claim 1 wherein the calcined alumina is present in the dentifrice at a concentration of about 2 to about 30% by weight.

5. The method of claim 1 wherein the phosphate salt is an alkali metal phosphate salt.

6. The method of claim 5 wherein the alkali metal phosphate salt is an alkali metal pyrophosphate.

7. The method of claim 5 wherein the alkali metal phosphate is an alkali metal polyphosphate.

8. The method of claim 5 wherein the alkali metal phosphate salt is a mixture of an alkali metal pyrophosphate and an alkali metal polyphosphate.

9. The method of claim 7 wherein the alkali metal pyrophosphate is sodium pyrophosphate and the alkali metal polyphosphate is sodium polyphosphate.

10. The method of claim 1 wherein a fluoride providing salt is present in the composition.

11. The method of claim 10 wherein the fluoride salt is sodium monofluorophosphate.

* * * * *